(12) United States Patent
Kocinska et al.

(10) Patent No.: US 10,123,956 B2
(45) Date of Patent: Nov. 13, 2018

(54) ORAL CARE COMPOSITIONS

(71) Applicant: Colgate-Palmolive Company, New York, NY (US)

(72) Inventors: Agnieszka Kocinska, Basel (CH); Pierre Lambert, Bottmingen (CH); Sandra Pereira Ramos, Sao Paulo (BR); Nadia Bueb, Rixheim (FR); Joshua Schmid, Laufen (CH)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/533,511

(22) PCT Filed: Dec. 23, 2014

(86) PCT No.: PCT/US2014/072189
§ 371 (c)(1),
(2) Date: Jun. 6, 2017

(87) PCT Pub. No.: WO2016/105389
PCT Pub. Date: Jun. 30, 2016

(65) Prior Publication Data
US 2017/0348212 A1    Dec. 7, 2017

(51) Int. Cl.
| *A61Q 11/00* | (2006.01) |
| *A61K 8/44* | (2006.01) |
| *A61K 8/24* | (2006.01) |
| *A61K 8/46* | (2006.01) |
| *A61K 8/19* | (2006.01) |
| *A61K 8/21* | (2006.01) |
| *A61K 8/34* | (2006.01) |
| *A61K 8/73* | (2006.01) |

(52) U.S. Cl.
CPC .................. *A61K 8/44* (2013.01); *A61K 8/19* (2013.01); *A61K 8/21* (2013.01); *A61K 8/24* (2013.01); *A61K 8/34* (2013.01); *A61K 8/463* (2013.01); *A61K 8/731* (2013.01); *A61Q 11/00* (2013.01); *A61K 2800/524* (2013.01)

(58) Field of Classification Search
CPC ....................................................... A61Q 11/00
See application file for complete search history.

(56) References Cited

U.S. PATENT DOCUMENTS

| 2009/0202450 A1 | 8/2009 | Prenicpe et al. |
| 2009/0202451 A1 | 8/2009 | Prenicpe et al. |
| 2009/0202455 A1 | 8/2009 | Kohli et al. |
| 2010/0330003 A1 | 12/2010 | Robinson et al. |
| 2011/0014136 A1 | 1/2011 | Kohli et al. |
| 2011/0052509 A1 | 3/2011 | Subramanyam et al. |
| 2011/0059029 A1 | 3/2011 | Kohli et al. |
| 2012/0141588 A1 | 6/2012 | Chopra et al. |
| 2013/0224270 A1 | 8/2013 | Robinson et al. |
| 2015/0297500 A1 | 10/2015 | Robinson et al. |

FOREIGN PATENT DOCUMENTS

| AU | 2012204031 | 7/2012 |
| CA | 2277664 | 1/2001 |
| EP | 2384739 | 11/2011 |
| EP | 2384740 | 11/2011 |
| WO | WO 1997/032565 | 9/1997 |
| WO | WO 2000/078270 | 12/2000 |
| WO | WO 2009/099452 | 8/2009 |
| WO | WO 2009/099453 | 8/2009 |
| WO | WO 2009/099455 | 8/2009 |
| WO | WO 2009/100263 | 8/2009 |
| WO | WO 2009/100268 | 8/2009 |
| WO | WO 2009/100279 | 8/2009 |
| WO | WO 2012/001337 | 1/2012 |
| WO | WO 2012/057739 | 5/2012 |
| WO | WO 2012/078337 | 6/2012 |
| WO | WO 2014/088575 | 6/2014 |

OTHER PUBLICATIONS

International Search Report and Written Opinion of the International Searching Authority in International Application No. PCT/US2014/072189, dated Aug. 5, 2015.

*Primary Examiner* — Benjamin J Packard

(57) ABSTRACT

An oral care composition comprising (i) basic amino acid in free or salt form, (ii) calcium carbonate, (iii) a fluoride ion source, (iv) a flavoring agent comprising less than 50% menthol, and (v) an anionic surfactant, wherein the anionic surfactant is present in an amount from 1.00 weight % to 1.39 weight % is provided.

27 Claims, No Drawings

ORAL CARE COMPOSITIONS

BACKGROUND

This invention relates to oral care compositions comprising a basic amino acid or salt together with calcium carbonate and a fluoride ion source, and to methods of using and of making these compositions.

Arginine and other basic amino acids have been proposed for use in oral care and are believed to have significant benefits in combating cavity formation and tooth sensitivity. It is also desirable to include the minerals fluoride and calcium in oral care compositions for their oral care benefits. Oral care compositions should be stable and maintain integrity when stored for a significant period of time.

Accordingly, there is a need for a stable oral care product comprising a basic amino acid, fluoride and calcium.

BRIEF SUMMARY

Although it is desirable to reduce the flavoring amount in dentifrice formulations for certain demographics such as children, the present inventors found that reduction in flavoring agent compromised the integrity of the final product. Further, attempts to improve this integrity with higher surfactant levels did not address the problem and in some instances increased the oil/water phase separation. However, when the surfactant level was lowered it was surprisingly found that stability increased. In turn, it has surprisingly been discovered that the combination of 1.00 weight % to 1.39 weight % anionic surfactant together with a basic amino acid, calcium carbonate, a flavoring agent comprising less than 50% menthol and a fluoride ion source provides a highly stable oral care formulation that can deliver excellent oral care benefits.

According to a first aspect of the invention there is provided an oral care composition comprising
  (i) a basic amino acid in free or salt form,
  (ii) calcium carbonate,
  (iii) a fluoride ion source,
  (iv) a flavoring agent comprising less than 50% menthol, and
  (v) an anionic surfactant,
wherein the anionic surfactant is present in an amount from 1.00 weight % to 1.39 weight %.

Optionally the oral care composition comprises a bacteriostatic preservative. Further optionally the oral care composition comprises benzyl alcohol. Further optionally the oral care composition comprises 0.25 weight % to 0.75 weight % benzyl alcohol. Further optionally the oral care composition comprises 0.45 weight % to 0.55 weight % benzyl alcohol.

Optionally the calcium carbonate is precipitated calcium carbonate. Further optionally the oral care composition comprises from 20 weight % to 60 weight % calcium carbonate. Further optionally the oral care composition comprises from 38 weight % to 44 weight % calcium carbonate. Further optionally the oral care composition comprises from 40 weight % to 43 weight % calcium carbonate.

Optionally the anionic surfactant is a water-soluble salt of a $C_{10}$ to $C_{18}$ alky sulfate. Further optionally the anionic surfactant is sodium lauryl sulfate. Further optionally the oral care composition comprises 1.05 weight % to 1.30 weight % sodium lauryl sulfate. Further optionally the oral care composition comprises 1.10 weight % to 1.25 weight % sodium lauryl sulfate. Further optionally the oral care composition comprises 1.14 weight % sodium lauryl sulfate.

Optionally the composition further comprises a flavoring agent. Optionally the composition comprises 0.1 weight % to 2.0 % flavoring agent. Further optionally the composition comprises 0.25 weight % to 1.1 % flavoring agent. Further optionally the oral care composition comprises 0.50 weight % flavoring agent. Optionally, the flavoring agent comprises menthol, carvone and/or anethole. Further optionally, the flavoring agent comprises oils of peppermint and spearmint. Optionally, the flavoring agent comprises less than 50% menthol, preferably less than 45% menthol, preferably less than 42% menthol.

Optionally the composition comprises a fluoride ion source selected from one or more of stannous fluoride, sodium fluoride, potassium fluoride, sodium monofluorophosphate, sodium fluorosilicate, ammonium fluorosilicate, amine fluoride, ammonium fluoride and combinations of one or more thereof. Further optionally the fluoride ion source comprises sodium monofluorophosphate. Further optionally the oral care composition comprises 0.90 weight % to 1.30 weight % sodium monofluorophosphate. Further optionally the oral care composition comprises 1.1 weight % sodium monofluorophosphate.

Optionally the composition comprises a basic amino acid selected from one or more of arginine, lysine, histidine, citrulline, ornithine, creatine, diaminobutanoic acid, diaminoproprionic acid, and salts and combinations thereof. Further optionally the oral care composition comprises a basic amino acid selected from arginine, citrulline, ornithine and salts thereof. Further optionally the oral care composition, comprises L-arginine or a salt thereof. Further optionally the oral care composition comprises 1.0 weight % to 5.0 weight % of a basic amino acid or salt thereof. Further optionally the composition comprises 1.5 weight % to 3.5 weight % L-arginine bicarbonate.

Optionally the composition comprises
  (i) 1.0 to 5.0 weight % of a basic amino acid in free or salt form
  (ii) 38 weight % to 44 weight % precipitated calcium carbonate
  (iii) 0.90 weight % to 1.30 weight % sodium monofluorophosphate
  (iv) 0.25 weight % to 1.0% flavoring agent comprising less than 50% menthol
  (v) 1.05 weight % to 1.3 weight % sodium lauryl sulfate.

Optionally the composition comprises
  (i) 1.0 to 5.0 weight % of a basic amino acid in free or salt form
  (ii) 38 weight % to 44 weight % precipitated calcium carbonate
  (iii) 0.90 weight % to 1.30 weight % sodium monofluorophosphate
  (iv) 0.25 weight % to 1.0% flavoring agent comprising less than 50% menthol
  (v) 1.05 weight % to 1.3 weight % sodium lauryl sulfate
  (vi) 0.65 weight % to 1.00 weight % sodium carboxymethylcellulose.

Optionally the oral care composition is a dentifrice. Further optionally the composition is a toothpaste or gel.

According to a further aspect of the invention there is provided a method to
  (i) reduce or inhibit formation of dental caries,
  (ii) reduce, repair or inhibit pre-carious lesions of the enamel,
  (iii) reduce or inhibit demineralization and promote remineralization of the teeth, (iv) reduce hypersensitivity of the teeth,
(v) reduce or inhibit gingivitis,
(vi) promote healing of sores or cuts in the oral cavity,
(vii) reduce levels of acid producing bacteria,
(viii) increase relative levels of arginolytic bacteria,
(ix) reduce or inhibit microbial biofilm formation in the oral cavity,
(x) reduce or inhibit plaque formation in the oral cavity,
(xi) promote systemic health,
(xii) clean teeth and oral cavity
comprising applying an effective amount of an oral care composition as herein described to the oral cavity of a subject in need thereof. Optionally the subject is a mammal. Further optionally the subject is a juvenile.

According to a further aspect of the invention there is provided an oral care composition as herein described for use in a method to
(i) reduce or inhibit formation of dental caries,
(ii) reduce, repair or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) increase relative levels of arginolytic bacteria,
(ix) reduce or inhibit microbial biofilm formation in the oral cavity,
(x) reduce or inhibit plaque formation in the oral cavity,
(xi) promote systemic health,
(xii) clean teeth and oral cavity.

According to a further aspect of the invention there is provided use of an oral care composition as herein described to
(i) reduce or inhibit formation of dental caries,
(ii) reduce, repair or inhibit pre-carious lesions of the enamel,
(iii) reduce or inhibit demineralization and promote remineralization of the teeth
in a subject in need thereof. Optionally the subject is a mammal. Further optionally the subject is a juvenile.

According to a further aspect of the invention there is provided a method for preparing an oral care composition as herein described comprising the sequential steps of
a. adding the basic amino acid to a solution comprising the fluoride ion source,
b. adding the calcium carbonate, and
c. adding the anionic surfactant.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

The composition may include a first feature described in one example herein, as well as a second feature described in another example herein. In other words, the invention contemplates mixing and matching features from the disclosed embodiments in various combinations.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

It has surprisingly been found that formulating an oral care composition comprising a basic amino acid, calcium ions and fluoride ions with 1.00 weight % to 1.39 weight % anionic surfactant results in a stable composition with excellent shelf life.

The oral care compositions of the present invention comprise a basic amino acid in free or salt form. The basic amino acids which can be used in the compositions and methods of the invention include not only naturally occurring basic amino acids such as arginine, lysine and histidine, but also any basic amino acids having a carboxyl group and an amino group in the molecule which are water-soluble and provide an aqueous solution with a pH of about 7 or greater. For example, basic amino acids may include but are not limited to arginine, lysine, citrulline, ornithine, creatine, histidine, diaminobutanoic acid, diamine propionic acid, salts thereof and combinations thereof. In certain embodiments the basic amino acid may comprise arginine, citrulline, ornithine and salts and combinations thereof. In certain embodiments the basic amino acid comprises arginine, for example L-arginine.

The basic amino acid may be in free or salt form. In certain embodiments, the basic amino acid is in salt form. Such salts should be pharmaceutically acceptable. In certain embodiments the basic amino acid is a salt derived from a pharmaceutically acceptable inorganic or organic acid or base, for example an acid addition salt formed by an acid which forms a physiologically acceptable anion, for example hydrochloride or bromide, or a base addition salt formed by a base which forms a physiologically acceptable cation such as an alkali metal or alkaline earth metal, for example potassium, sodium, calcium or magnesium. In certain embodiments the basic amino acid is a bicarbonate salt of an amino acid. For example, the basic amino acid may be arginine bicarbonate. In certain embodiments the basic amino acid is L-arginine bicarbonate.

In certain embodiments the basic amino acid in free or salt form is present in an amount from 0.5 weight % to 5.0 weight % based on the total weight of the composition. In certain embodiments the basic amino is present in an amount of from 0.5 weight % to 3.0 weight %, from 1.0 weight % to 2.5 weight % or from 1.2 weight % to 2.0 weight %. In certain embodiments the basic amino acid is present in an amount of 1.5 weight %. In certain embodiments the basic amino acid in salt form is present in an amount of from 1.0 weight % to 4.0 weight %, from 1.5 weight % to 3.5 weight %, from 2.0 weight % to 3.5 weight % or from 2.0 weight % to 3.0 weight %. In certain embodiments the basic amino acid in salt form is present in an amount of about 2.7 weight %.

In certain embodiments the composition comprises from 0.5 weight % to 5.0 weight % arginine, for example 1.0 weight % to 4.0 weight % arginine, 1.0 weight % to 2.0 weight % or about 1.5 weight % arginine. In certain embodiments the composition comprises L- or D-arginine in free or salt form. In certain embodiments the composition comprises L-arginine in free or salt form.

In certain embodiments the composition comprises arginine bicarbonate in an amount from 1.0 weight % to 5.0 weight % based on the total weight of the composition. In certain embodiments the arginine bicarbonate is present in an amount of from 1.5 weight % to 4.0 weight %, from 1.5 weight % to 3.5 weight, from 2.0 weight % to 3.5 weight % or from 2.0 weight % to 3.0 weight %. In certain embodiments the arginine bicarbonate is present in an amount of about 2.7 weight %. In certain embodiments the composition comprises L-arginine bicarbonate.

The compositions of the invention comprise calcium carbonate. Natural calcium carbonate is found in rocks such as chalk, limestone, marble and travertine, as well as egg shells and mollusk shells. Natural calcium carbonate can be used as an abrasive in oral care compositions. Typically, natural calcium carbonate abrasive is finely ground limestone which may optionally be refined or partially refined to remove impurities. In certain embodiments, the natural calcium carbonate has an average particle size of less than 10 microns, for example 3 to 7 microns or about 5.5 microns.

In certain embodiments the composition comprises precipitated calcium carbonate. Precipitated calcium carbonate (PCC) is generally made by calcining limestone to make oxide (lime) which can then be converted back to calcium carbonate by reaction with carbon dioxide in water. Precipitated calcium carbonate has a different crystal structure from natural calcium carbonate. It is generally more friable and more porous, thus having lower abrasivity and higher water absorption. In certain embodiments, the calcium carbonate comprises precipitated calcium carbonate with an average particle size of 1 to 5 microns and for example no more than 0.1% or preferably 0.05% by weight of particles which would not pass through a 325 mesh. In certain embodiments, the PCC particles have a $D_{90}$ of 3 to 10 microns, for example about 3.4 to about 9.0 microns (Sedigraph). In certain embodiments the PCC particles have a $D_{90}$ of about 4.3 microns. In certain embodiments the PCC particles have a $D_{50}$ of 1 to 7 microns, for example about 1.5 to about 4.0 microns (Sedigraph). In certain embodiments the PCC particles have a $D_{50}$ of about 2.4 microns. In certain embodiments the PCC particles have a D10 of about 0.3 to about 1.30 microns (Sedigraph), for example a $D_{10}$ of 1 to 2 microns. In certain embodiments the PCC particles have a D10 of about 1.3 microns. In certain embodiments the PCC particles have a $D_{50}$ by Sedigraph of 1.87 to 1.93 microns and a $D_{90}$ by Sedigraph of 3.45 to 3.55 microns. In certain embodiments the PCC particles have particle size by Malvern of $D_{10}$ 1.10-1.70, $D_{50}$ 5.00-7.00 and $D_{90}$ 10.50-14.50 microns. In certain embodiments the PCC particles have particle size by Sedigraph of $D_{10}$ 0.3-1.30, $D_{50}$ 2.50-4.00 and $D_{90}$ 6.00-9.00 microns. In certain embodiments the PCC particles have particle sizes by Beckman Coulter of $D_{10}$ 0.22-0.49, $D_{50}$ 4.10-5.90 and $D_{90}$ 9.70-12.90 microns. In certain embodiments the PCC particles have particle size by Malvern of $D_{10}$ 0.60-1.20, $D_{50}$ 3.50-6.00 and $D_{90}$ 7.00-12.00 microns. In certain embodiments the PCC particles have particle size by Cilag of $D_{10}$ 0.30-0.90, $D_{50}$ 3.00-5.00 and $D_{90}$ 5.50-8.50 microns. In certain embodiments the PCC particles have particle size by Beckman Coulter of $D_{10}$ 0.15-0.22, $D_{50}$ 2.80-4.20 and $D_{90}$ 5.00-9.70 microns. In certain embodiments the PCC particles have a high water absorption. In certain embodiments the PCC particles have a water absorption of 15-70 g/100 g, for example 15 to 26 g/100 g or 17 to 20 g/100 g.

In certain embodiments the composition comprises additional calcium-containing abrasives, for example a calcium phosphate abrasive such as tricalcium phosphate, hydroxyapatite or dicalcium phosphate dehydrate. In certain embodiments the composition comprises silica abrasives such as precipitated silicas having a mean particle size of up to about 20 μm, sodium metaphosphate, potassium metaphosphate, aluminium silicate, calcined alumina, bentonite or other siliceous materials and/or combinations thereof.

In certain embodiments, the composition comprises from 20 to 60 weight % calcium carbonate, for example from 30 to 50 weight %, from 35 to 45 weight % or from 38 to 44 weight %. In certain embodiments the composition comprises from 40 to 43 weight %, for example from 41 to 42 weight %.

In certain embodiments, the composition comprises from 40 to 43 weight % precipitated calcium carbonate.

The compositions of the present invention comprises a fluoride ion source. In certain embodiments, the composition comprises one or more fluoride ion sources, for example soluble fluoride salts. In certain embodiments the composition comprises a fluoride ion source selected from one or more of stannous fluoride, sodium fluoride, potassium fluoride, sodium monofluorophosphate, sodium fluorosilicate, ammonium, fluorosilicate, amine fluoride, ammonium fluoride and combinations of one or more thereof.

In certain embodiments, the composition comprises sodium monofluorophosphate.

In certain embodiments, the composition comprises a fluoride ion source in an amount sufficient to supply about 25 ppm to about 25,000 ppm fluoride ions, for example from about 500 ppm to about 200 ppm, from about 1000 ppm to about 1600 ppm.

The weight of fluoride salt may be selected in order to provide the appropriate level of fluoride ion in the formulation. In certain embodiments the composition comprises about 0.01 weight % to about 10 weight % fluoride ion source, for example about 0.03 to about 5.0 weight %, or about 0.1 to about 1.0 weight %.

In certain embodiments the composition comprises about 0.03 to about 5.0 weight % sodium monofluorophosphate, for example about 0.5 to about 2.0 weight %, from 0.90 to about 1.30 weight % or from about 1.80 to about 1.30 weight % sodium monofluorophosphate.

The compositions of the invention comprise 1.00 to 1.39 weight % anionic surfactant. It has surprisingly been discovered that this level of anionic surfactant stabilizes formulations comprising a basic amino acid, calcium carbonate and fluoride.

In certain embodiments, the composition comprises an anionic surfactant that comprises a water-soluble salt of a $C_{10}$ to $C_{18}$ alkyl sulfate. In certain embodiments, the composition comprises one or more surfactant selected from sodium lauryl sulfate, sodium lauroyl sarcosinate and sodium coconut monoglyceride sulfonates. In certain embodiments the composition comprises a mixture of one or more anionic surfactants.

In certain embodiments, the composition comprises from 1.00 to 1.30 weight % anionic surfactant, for example from 1.05 to 1.25 weight %, from 1.15 to 1.25 weight % or about 1.20 weight % anionic surfactant. In certain embodiments, the composition comprises from 1.05 to 1.25 weight %, from 1.15 to 1.25 weight % or about 1.20 weight % sodium lauryl sulfate. In certain embodiments the composition comprises 95% sodium lauryl sulfate in an amount of from 1.05 weight % to 1.30 weight %, from 1.10 weight % to 1.25 weight % or about 1.14 weight %.

In certain embodiments the compositions of the present invention comprise a flavoring agent. The flavoring agent may comprise one or more essential oils as well as various flavoring aldehydes, esters and/or alcohols. In certain embodiments, the flavoring agent comprises one or more essential oil selected from oils of peppermint, wintergreen, sassafras, clove, sage, eucalyptus, marjoram, cinnamon, lemon, lime, grapefruit and orange. In certain embodiments, the flavoring agent comprises menthol, carvone and/or anethole. In certain embodiments, the flavoring agent comprises oils of peppermint and spearmint. In certain embodiments, the flavoring agent comprises less than 50% menthol, preferably less than 45% menthol, preferably less than 42% menthol.

In certain embodiments the composition comprises 0.1 to 2.0 weight %, 0.25 to 1.5 weight %, 0.25 weight % to 1.1 weight %, 0.30 weight % to 0.8 weight %, 0.40 weight % to 0.60 weight % or about 0.50 weight % flavoring agent. In certain embodiments the composition comprises a flavoring agent in an amount acceptable to juveniles. In certain embodiments the composition comprises a flavoring agent in an amount that is lower than that provided in an adult formulation in order to provide a gentler flavor to the consumer.

In certain embodiments, the composition comprises a bacteriostatic preservative. In certain embodiments, the composition comprises benzyl alcohol. In certain embodiments the composition comprises 0.25 weight % to 0.75 weight %, 0.35 weight % to 0.60 weight % or 0.40 weight % to 0.60 weight % bacteriostatic preservative. In certain embodiments the composition comprises 0.25 weight % to 0.75 weight %, 0.35 weight % to 0.60 weight % or 0.40 weight % to 0.60 weight % benzyl alcohol. In certain embodiments the composition comprises about 0.50 weight % benzyl alcohol. In certain embodiments the composition comprises more than 0.30 weight % benzyl alcohol as preservative in order to increase the microrobustness of the composition.

In certain embodiments the composition comprises a reduced amount of flavoring agent and an increased amount of bacteriostatic preservative. In certain embodiments the composition comprises more than 0.30 weight % preservative and no more than 0.8 weight % flavoring agent. In certain embodiments the composition comprises 0.4 weight % to 0.6 weight % benzyl alcohol and 0.3 weight % to 0.7 weight % flavoring agent.

In certain embodiments the composition comprises 1.0 to 5.0 weight % of a basic amino acid in free or salt form, 38 weight % to 44 weight % precipitated calcium carbonate, 0.90weight % to 1.30 weight % sodium monofluorophosphate, 0.25 weight % to 1.0% flavoring agent and 1.10 weight % to 1.30 weight % sodium lauryl sulfate. In certain embodiments the composition comprises 1.0 to 5.0 weight % of a basic amino acid in free or salt form, 38 weight % to 44 weight % precipitated calcium carbonate, 0.90 weight % to 1.30 weight % sodium monofluorophosphate, 0.25 weight % to 1.0% flavoring agent, 1.10 weight % to 1.30 weight % sodium lauryl sulfate and 0.35 weight % to 0.60 weight % benzyl alcohol.

In certain embodiments the composition is a toothpaste, transparent paste, or gel. In certain embodiments the composition is a dentifrice such as a toothpaste or gel.

In certain embodiments the composition may comprise one or more chelating agents. In certain embodiments the composition comprises one or more chelating agent able to complex calcium found in the cell walls of bacteria. In certain embodiments the composition comprises one or more soluble pyrophosphate as chelating agent. In certain embodiments the pyrophosphate salts can be any of the alkali metal pyrophosphate salts. In certain embodiments the salts include tetra alkali metal pyrophosphate, dialkali metal diacid pyrophosphate, trialkali metal monoacid pyrophosphate and mixtures thereof wherein the alkali metals are sodium or potassium. In certain embodiments the composition comprises such pyrophosphate salts in an amount to provide at least about 1 weight % pyrophosphate ions, for example about 1.5 weight % to about 6 weight % or about 3.5 weight % to about 6 weight %.

In certain embodiments the compositions of the invention include one or more polymers such as polyethylene glycols, polyvinylmethyl ether maleic acid copolymers and polysaccharides (e.g. cellulose derivatives such as carboxymethyl cellulose or microcrystalline cellulose, or polysaccharide gums such as xanthan gum or carrageenan gum). Acidic polymers, for example polyacrylate gels, may be provided as free acids or partially or fully neutralized water soluble alkali metal (e.g. potassium and sodium) or ammonium salts.

In certain embodiments the composition comprises about 0.05 to about 5% of an agent which enhances the delivery and retention of oral care agents to and retention thereof on oral surfaces. In certain embodiments the composition comprises synthetic anionic polymeric polycarboxylates such 1:4 to 4:1 copolymers of maleic anhydride or acid with another polymerizable ethylenically unsaturated monomer, preferably methyl vinyl ether/maleic anhydride having a molecular weight of about 30,000 to about 1,000,000. In certain embodiments the composition comprises from about 0.05 to about 3% by weight of such agents. In certain embodiments the composition comprises a thickening material to enhance the performance of the formulation. In certain embodiments the thickening agents are carboxyvinyl polymers, carrageenan, hydroxyethyl cellulose and water soluble salts of cellulose ethers such as sodium carboxy methyl cellulose and sodium carboxymethyl hydroxyethyl cellulose. Natural gums such as karaya, gum arabic and gum tragacanth may also be included. In certain embodiments the composition comprises colloidal magnesium aluminium silicate or finely divided silica. In certain embodiments a thickening agent is present in an amount of about 0.5 to about 5.0%. In certain embodiments the composition comprises from about 0.5 to about 5% cellulose gum.

In certain embodiments the composition comprises from 1.00 to 1.30 weight % anionic surfactant together with 0.5 weight % to 1.5 weight % sodium carboxymethyl cellulose. In certain embodiments, the composition comprises from 1.05 to 1.25 weight %, sodium lauryl sulfate and 0.65 weight % to 1.00 weight % sodium carboxymethyl cellulose.

In certain embodiments the composition comprises one or more humectants. Humectants can prevent the composition from hardening upon exposure to air. In certain embodiments the composition comprises one or more humectants selected from edible poiyhydric alcohols such as glycerine, sorbitol, xylitol, propylene glycol and mixtures thereof. In certain embodiments the composition comprises from about 5 to about 25% humectant. In certain embodiments the composition comprise from about 5 to about 25% glycerine.

The compositions of the invention can be used to protect teeth by facilitating repair and remineralization. In particular the compositions of the invention can be used reduce or inhibit formation of dental caries, reduce, repair or inhibit pre-carious lesions of the enamel, reduce or inhibit demineralization and promote remineralization of the teeth, reduce hypersensitivity of the teeth, reduce or inhibit gingivitis, promote healing of sores or cuts in the oral cavity, reduce levels of acid producing bacteria, increase relative levels of arginolytic bacteria, reduce or inhibit microbial biofilm formation in the oral cavity, reduce or inhibit plaque formation in the oral cavity, promote systemic health, clean teeth and oral cavity.

In certain embodiments, the compositions of the invention can be used in methods to enhance oral health and thereby provide benefits in systemic health. Good oral health is associated with systemic health including cardiovascular health. Basic amino acids, especially arginine, are sources of nitrogen which NO synthesis pathways and thus enhance microcirculation in the oral tissues. Providing a less acidic oral environment is also helpful in reducing gastric distress and creates an environment less favourable to Heliobacter which is associated with gastric ulcers. Arginine in particular is required for high expression of specific immune cell receptors, for example T-cell receptors, so that arginine can enhance an effective immune response. The compositions and methods of the invention are thus useful to enhance systemic health, including cardiovascular health.

In certain embodiments of the invention, the composition is applied to the oral cavity using a manual or electric toothbrush.

In certain embodiments, the composition is applied to the oral cavity of a mammal. In certain embodiments the composition is applied to the oral cavity of a juvenile mammal. In certain embodiments the composition is applied to the oral cavity of a human subject under the age of 18 years.

The compositions of the invention can provide excellent anti-cavity protection whilst also possessing good stability and product integrity.

EXAMPLES

A dentifrice composition Formulation A according to Table 1 was prepared:

TABLE 1

| Formulation A | |
|---|---|
| INGREDIENT | WEIGHT % |
| Purified water and colour | 33.7 |
| Glycerin | 16.1 |
| Sodium carboxymethylcellulose | 1.04 |
| Sodium saccharin | 0.40 |
| Sodium hydroxide 50% | 0.10 |
| Sodium monofluorophosphate | 1.10 |
| Tetrasodium pyrophosphate | 0.50 |
| Benzyl alcohol | 0.50 |
| Sodium bicarbonate | 0.50 |
| Precipitated calcium carbonate | 41.0 |
| Sodium lauryl sulfate 95% | 1.85 |
| Arginine bicarbonate | 2.67 |
| Flavor (41% menthol) | 0.50 |

This formulation was found to suffer from phase separation and to lack stability. Formulation A was subjected to an ageing stability study. The formulation was stored in a laminate container under various conditions and assessed at various time points for viscosity and appearance (whiteness). Appearance was assessed on a scale of whiteness from 0 (worst) to 4 (best). The results are shown in Table 2:

TABLE 2

| Conditions | Time (weeks) | Viscosity (×10,000 cps) | Appearance (0-4) |
|---|---|---|---|
| −30° C. | 8 | — | FAIL (1) |
| 25° C. 60% relative humidity | 0 | 25 | PASS (4) |
| 25° C. 60% relative humidity | 4 | CANCELLED | PASS (2) |
| 25° C. 60% relative humidity | 8 | CANCELLED | FAIL (1) |
| 25° C. 60% relative humidity | 13 | CANCELLED | FAIL (1) |
| 40° C. 75% relative humidity | 4 | CANCELLED | FAIL (1) |
| 40° C. 75% relative humidity | 8 | CANCELLED | FAIL (1) |
| 40° C. 75% relative humidity | 13 | CANCELLED | FAIL (1) |

Viscosity is measured using a Brookfield Viscometer (RVT or RVTDV) at controlled room temperature (75-77° F./24-25° C.) using T-E spindle at 5 rpm. Readings are converted to viscosity in centipoise by multiplying by 10,000 for T-E spindle at 5 rpm.

A dentifrice composition Formulation B according to the present invention was prepared. This formulation is provided in Table 3:

TABLE 3

| Formulation B | |
|---|---|
| INGREDIENT | WEIGHT % |
| Purified water and colour | 34.6 |
| Glycerin | 16.1 |
| Sodium carboxymethylcellulose | 0.80 |
| Sodium saccharin | 0.40 |
| Sodium hydroxide 50% | 0.10 |
| Sodium monoflurorophosphate | 1.10 |
| Tetrasodium pyrophosphate | 0.50 |
| Benzy alcohol | 0.50 |
| Sodium bicarbonate | 0.50 |
| Precipitated calcium carbonate | 41.0 |
| Sodium lauryl sulfate 95% | 1.20 |
| Arginine bicarbonate | 2.67 |
| Flavor (41% menthol) | 0.50 |

Formulation B was found to possess excellent formulation properties with good structure and no oily separation. This contrasts with formulations comprising an increased level of sodium lauryl sulfate of 1.75 or 1.80 weight % which were observed to suffer from oily separation.

Formulation B was also subjected to an ageing stability study. The formulation was stored in a laminate container under various conditions and assessed at various time points for viscosity and appearance (whiteness). Once again appearance was assessed on a scale of whiteness from 0 (worst) to 4 (best). The results are shown in Table 4:

TABLE 4

| Conditions | Time (weeks) | Viscosity (×10,000 cps) | Appearance (0-4) |
|---|---|---|---|
| −30° C. | 8 | — | PASS (4) |
| 25° C. 60% relative humidity | 0 | 30 | PASS (4) |
| 25° C. 60% relative humidity | 4 | 48 | PASS (4) |
| 25° C. 60% relative humidity | 8 | 53 | PASS (4) |

TABLE 4-continued

| Conditions | Time (weeks) | Viscosity (×10,000 cps) | Appearance (0-4) |
|---|---|---|---|
| 25° C. 60% relative humidity | 13 | 64 | PASS (4) |
| 40° C. 75% relative humidity | 4 | 53 | PASS (3) |
| 40° C. 75% relative humidity | 8 | 67 | PASS (4) |
| 40° C. 75% relative humidity | 13 | 62 | PASS (4) |

Viscosity is measured using a Brookfield Viscometer (RVT or RVTDV) at controlled room temperature (75-77° F./24-25° C.) using T-E spindle at 5 rpm. Readings are converted to viscosity in centipoise by multiplying by 10,000 for T-B spindle at 5 rpm.

The stability of Formulation B was also compared to Formulation C comprising a similar level of sodium carboxymethyl cellulose, but a higher level of sodium lauryl sulfate.

TABLE 5

Formulation C

| INGREDIENT | WEIGHT % |
|---|---|
| Purified water and colour | 34.22 |
| Glycerin | 16.1 |
| Sodium carboxymethylcellulose | 0.60 |
| Sodium saccharin | 0.4 |
| Sodium hydroxide 50% | 0.1 |
| Sodium monofluorophosphate | 1.1 |
| Tetrasodium pyrophosphate | 0.5 |
| Benzyl alcohol | 0.5 |
| Sodium bicarbonate | 0.5 |
| Precipitated calcium carbonate | 41 |
| Sodium lauryl sulfate 95% | 1.81 |
| Arginine bicarbonate | 2.67 |
| Flavor (41% menthol) | 0.50 |

Formulation C was subjected to an ageing stability study. As before, the formulation was stored in a laminate container under various conditions and assessed at various time points for viscosity and appearance (whiteness). Once again appearance was assessed on a scale of whiteness from 0 (worst) to 4 (best). The results are shown in Table 6:

TABLE 6

| Conditions | Time (weeks) | Viscosity (×10,000 cps) | Appearance (0-4) |
|---|---|---|---|
| 25° C. 60% relative humidity | 0 | 23.3 | PASS (4) |
| 25° C. 60% relative humidity | 4 | 38 | PASS (3) |
| 25° C. 60% relative humidity | 8 | N/A | FAIL (1) |
| 25° C. 60% relative humidity | 13 | CANCELLED | CANCELLED |
| 40° C. 75% relative humidity | 4 | 33 | PASS (3) |
| 40° C. 75% relative humidity | 8 | N/A | FAIL (1) |
| 40° C. 75% relative humidity | 13 | CANCELLED | CANCELLED |
| 49° C. | 4 | N/A | PASS (3) |
| 49° C. | 6 | CANCELLED | CANCELLED |
| 49° C. | 8 | N/A | FAIL (1) |
| 49° C. | 13 | CANCELLED | CANCELLED |
| 4° C. | 4 | N/A | PASS (3) |
| 4° C. | 8 | N/A | FAIL (1) |
| 4° C. | 13 | N/A | CANCELLED |

Viscosity is measured using a Brookfield Viscometer (RVT or RVTDV) at controlled room temperature (75-77° F./24-25° C.) using T-E spindle at 5 rpm. Readings are converted to viscosity in centipoise by multiplying by 10,000 for T-E spindle at 5 rpm.

The results of this ageing stability study show that this formulation also suffers from phase separation and lacks stability.

What is claimed is:

1. An oral care composition comprising
   (i) basic amino acid in free or salt form,
   (ii) calcium carbonate,
   (iii) a fluoride ion source,
   (iv) a flavoring agent comprising less than 50% menthol and
   (v) an anionic surfactant,
wherein the anionic surfactant is present in an amount from 1.00 weight % to 1.39 weight %, and the flavoring agent is present in an amount from 0.3 weight % to 0.8 weight %.

2. The oral care composition of claim 1 further comprising a bacteriostatic preservative.

3. The oral care composition of claim 1 further comprising benzyl alcohol.

4. The oral care composition of claim 1 further comprising 0.25 weight % to 0.75 weight % benzyl alcohol.

5. The oral care composition of claim 1 wherein the calcium carbonate is precipitated calcium carbonate.

6. The oral care composition of claim 1 wherein the composition comprises from 20 weight % to 60 weight % calcium carbonate.

7. The oral care composition of claim 1 wherein the anionic surfactant is a water-soluble salt of a $C_{10}$ to $C_{18}$ alkyl sulfate.

8. The oral care composition of claim 1 wherein the anionic surfactant is sodium lauryl sulfate.

9. The oral care composition of claim 1 wherein the composition comprises 1.05 weight % to 1.30 weight % sodium lauryl sulfate.

10. The oral care composition of claim 1 wherein the flavoring agent comprises less than 45% menthol.

11. The oral care composition of claim 1 wherein the composition comprises a fluoride ion source selected from one or more of stannous fluoride, sodium fluoride, potassium fluoride, sodium monofluorophosphate, sodium fluorosilicate, ammonium fluorosilicate, amine fluoride, ammonium fluoride and combinations of one or more thereof.

12. The oral care composition of claim 1 wherein the fluoride ion source comprises sodium monofluorophosphate.

13. The oral care composition of claim 1 wherein the composition comprises 0.90 weight % to 1.30 weight % sodium monofluorophosphate.

14. The oral care composition of claim 1 wherein the composition comprises a basic amino acid selected from one or more of arginine, lysine, histidine, citrulline, ornithine, creatine, diaminobutanoic acid, diaminoproprionic acid, and salts and combinations thereof.

15. The oral care composition of claim 1 wherein the composition comprises a basic amino acid selected from arginine, citrulline, ornithine and salts and combinations thereof.

16. The oral care composition of claim 1 wherein the composition comprises L-arginine or a salt thereof.

17. The oral care composition of claim 1 wherein the composition comprises 1.0 weight % to 5.0 weight % of a basic amino acid or salt thereof.

18. The oral care composition of claim 1 wherein the composition comprises 1.5 weight % to 3.5 weight % L-arginine bicarbonate.

19. The oral care composition of claim 1 wherein the composition comprises
   (i) 1.0 to 5.0 weight % of a basic amino acid in free or salt form
   (ii) 38 weight % to 44 weight % precipitated calcium carbonate
   (iii) 0.90 weight % to 1.30 weight % sodium monofluorophosphate
   (iv) 0.25 weight % to 1.0% flavoring agent comprising less than 50% menthol
   (v) 1.05 weight % to 1.30 weight % sodium lauryl sulfate.

20. The oral care composition of claim 1 wherein the composition comprises
   (i) 1.0 to 5.0 weight % of a basic amino acid in free or salt form
   (ii) 38 weight % to 44 weight % precipitated calcium carbonate
   (iii) 0.90 weight % to 1.30 weight % sodium monofluorophosphate
   (iv) 0.25 weight % to 1.0% flavoring agent comprising less than 50% menthol
   (v) 1.05 weight % to 1.30 weight % sodium lauryl sulfate
   (vi) 0.65 weight % to 1.00 weight % sodium carboxymethylcellulose.

21. The oral care composition of claim 1 wherein the composition is a dentifrice.

22. The oral care composition of claim 1 wherein the composition is a toothpaste or gel.

23. A method to
   (i) reduce or inhibit formation of dental caries,
   (ii) reduce, repair or inhibit pre-carious lesions of the enamel,
   (iii) reduce or inhibit demineralization and promote remineralization of the teeth,
   (iv) reduce hypersensitivity of the teeth,
   (v) reduce or inhibit gingivitis,
   (vi) promote healing of sores or cuts in the oral cavity,
   (vii) reduce levels of acid producing bacteria,
   (viii) increase relative levels of arginolytic bacteria,
   (ix) reduce or inhibit microbial biofilm formation in the oral cavity,
   (x) reduce or inhibit plaque formation in the oral cavity,
   (xi) promote systemic health,
   (xii) clean teeth and oral cavity,
comprising applying an effective amount of an oral care composition according to claim 1 to the oral cavity of a subject in need thereof.

24. The method of claim 23 wherein the subject is a mammal.

25. The method of claim 23 wherein the subject is a juvenile.

26. An oral care composition according to claim 1 for use in a method to
   i) reduce or inhibit formation of dental caries,
   ii) reduce, repair or inhibit pre-carious lesions of the enamel,
   iii) reduce or inhibit demineralization and promote remineralization of the teeth,
   iv) reduce hypersensitivity of the teeth,
   v) reduce or inhibit gingivitis,
   vi) promote healing of sores or cuts in the oral cavity,
   vii) reduce levels of acid producing bacteria,
   viii) increase relative levels of arginolytic bacteria,
   ix) reduce or inhibit microbial biofilm formation in the oral cavity,
   x) reduce or inhibit plaque formation in the oral cavity,
   xi) promote systemic health,
   xii) clean teeth and oral cavity.

27. A method for preparing an oral care composition according to claim 1 comprising the sequential steps of
   (i) adding the basic amino acid to a solution comprising the fluoride ion source,
   (ii) adding the calcium carbonate,
   (iii) adding the anionic surfactant.

* * * * *